United States Patent [19]

Leppard et al.

[11] Patent Number: 4,518,688
[45] Date of Patent: May 21, 1985

[54] COLOR-PHOTOGRAPHIC RECORDING MATERIAL

[75] Inventors: David G. Leppard, Marly; Jean Rody, Riehen, both of Switzerland

[73] Assignee: Ciba-Geigy AG, Basel, Switzerland

[21] Appl. No.: 555,633

[22] Filed: Nov. 25, 1983

[30] Foreign Application Priority Data

Nov. 26, 1982 [CH] Switzerland .................. 6894/82

[51] Int. Cl.$^3$ .............................. G03C 7/26
[52] U.S. Cl. ................... 430/551; 430/216; 430/372; 430/505; 430/523; 430/961
[58] Field of Search ............ 430/372, 551, 505, 216, 430/523, 961

[56] References Cited

U.S. PATENT DOCUMENTS 4,185,007  1/1980  Rasberger et al. ............... 524/101
4,268,593  5/1981  Leppard et al. ................. 430/372
4,452,884  6/1984  Leppard ........................ 430/372

Primary Examiner—J. Travis Brown
Attorney, Agent, or Firm—Wenderoth, Lind & Ponack

[57] ABSTRACT

Compounds of the formula I

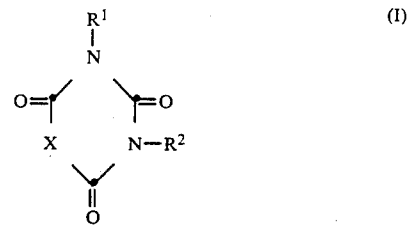

in which X is a group

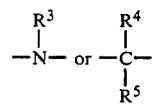

and $R^1$, $R^2$, $R^3$, $R^4$ and $R^5$ are monovalent organic radicals, at least one of which contains a sterically hindered phenol group and at least one of which contains a polyalkylpiperidine group, are outstanding light stabilizers for color-photographic recording materials. They also have a stabilizing action on the photo dyes and their precursors when stored in the dark.

10 Claims, No Drawings

COLOR-PHOTOGRAPHIC RECORDING MATERIAL

The present invention relates to a colour-photographic recording material containing, as a stabiliser, a specific heterocyclic compound in at least one light-sensitive silver halide emulsion layer and/or in at least one of the conventional auxiliary layers. These compounds are isocyanuric acid derivatives or barbituric acid derivatives, the molecule of which contains both a sterically hindered phenol group and a polyalkylpiperidine group.

Molecules which combine sterically hindered phenols and polyalkylpiperidines and which can be used as stabilisers for colour-photographic materials are already known from European Pat. No. A 11,051. These are polyalkylpiperidinyl esters of hydroxybenzylmalonic acids. In following up this research work further it has been found that certain heterocyclic compounds containing sterically hindered phenol groups and piperidine groups also possess an excellent light-stabilising action for colour photographs and, in addition, also stabilise the dyes in the dark against changes which occur when the recording material is stored.

The present invention relates, therefore, to a colour-photographic recording material which, in at least one light-sensitive silver halide emulsion layer, one intermediate layer, one image-receiving layer and/or one protective layer, contains, as a stabiliser, at least one compound of the formula I

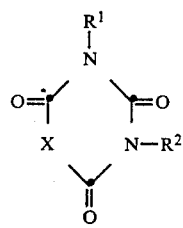
(I)

in which X is a group

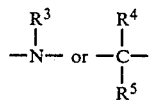

and $R^1$, $R^2$, $R^3$, $R^4$ and $R^5$ are monovalent organic radicals, at least one of which contains a sterically hindered phenol group and at least one of which contains a polyalkylpiperidine group.

These stabilisers are, in particular, compounds of the formula I in which X is a group —N($R^3$)— or —C($R^4$)($R^5$)—, $R^1$, $R^2$ and $R^3$ independently of one another are either (a) a group of the formula II

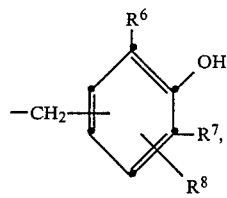
(II)

in which $R^6$ is hydrogen, $C_1$–$C_8$-alkyl, $C_5$–$C_8$-cycloalkyl, $C_7$–$C_9$-phenylalkyl, phenyl or $C_7$–$C_{10}$-alkylphenyl, $R^7$ is $C_1$–$C_8$-alkyl, $C_5$–$C_8$-cycloalkyl, $C_7$–$C_9$-phenylalkyl, phenyl or $C_7$–$C_{10}$-alkylphenyl, and $R^8$ is hydrogen or methyl, or (b) a group of the formula III or IV

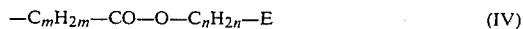

in which m is 1–4 and n is 2–5, Y is —O— or —$NR^9$— and $R^9$ is hydrogen, $C_1$–$C_{12}$-alkyl, $C_5$–$C_{12}$-cycloalkyl, $C_3$–$C_{12}$-alkoxyalkyl, $C_4$–$C_{12}$-dialkylaminoalkyl or a group of the formula

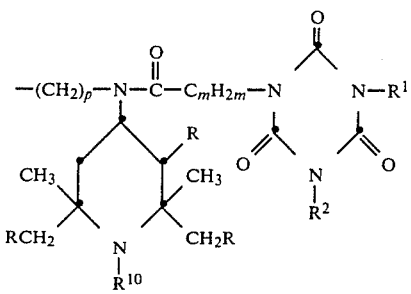

in which p is 2–12, or $R^9$ is D, D is a group of the formula V, VI or VII

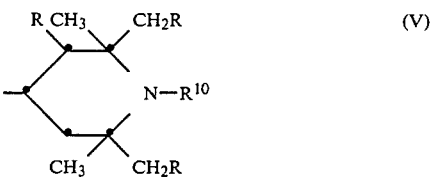
(V)

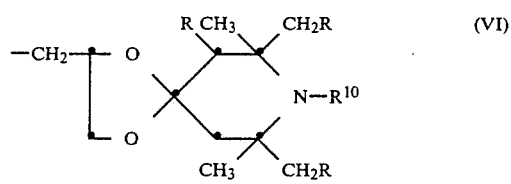
(VI)

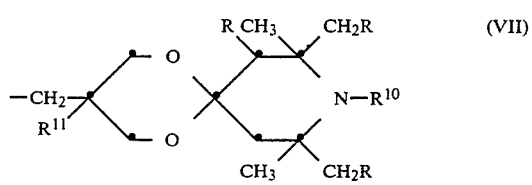
(VII)

and E is a group of the formula VIII

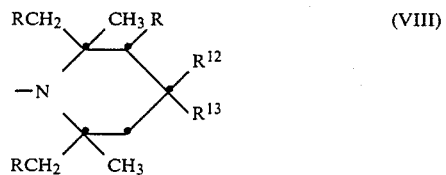
(VIII)

in which R is hydrogen or methyl, $R^{10}$ is hydroxyl, $C_1$–$C_{12}$-alkyl, $C_3$–$C_6$-alkenyl, $C_3$–$C_4$-alkinyl, $C_7$–$C_{12}$-phenylalkyl, glycidyl, $C_1$–$C_4$-alkyl which is substituted by halogen, —CN, —$COOR^{15}$ or —CON($R^{16}$)($R^{17}$), or a group —CO—$R^{18}$—CO—$OR^{15}$, —CO—N($R^{16}$)($R^{17}$), —$CH_2$—CH($R^{19}$)—$OR^{20}$, —SO—$R^{21}$, —$SO_2$—$R^{21}$, —$OR^{15}$ or —$OOC$—$R^{18}$, $R^{11}$ is methyl or ethyl, $R^{12}$ is hydrogen, —$OR^{22}$, —$OOC$—$R^{18}$ or —$N(R^9)$—$CO$—$R^{18}$ and $R^{13}$ is hydrogen, —$CN$, —$COOR^{15}$ or —$CONH_2$ or $R^{12}$ and $R^{13}$ together form a group of the following formulae

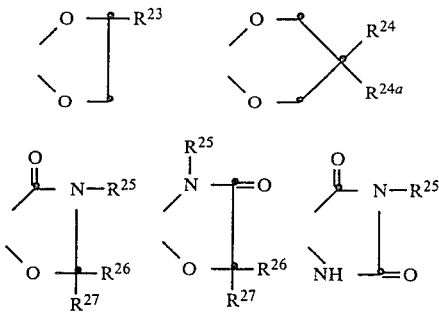

$R^{15}$ is $C_1$–$C_{12}$-alkyl, allyl, benzyl or cyclohexyl, $R^{16}$ is $C_1$–$C_{12}$-alkyl, allyl, cyclohexyl, benzyl or phenyl, and $R^{17}$ is hydrogen or $C_1$–$C_8$-alkyl, or $R^{16}$ and $R^{17}$, together with the N atom, are a 5-membered or 6-membered heterocyclic ring, $R^{18}$ is hydrogen, $C_1$–$C_{12}$-alkyl, $C_2$–$C_6$-alkenyl, chloromethyl, $C_5$–$C_{12}$-cycloalkyl, $C_7$–$C_{12}$-phenylalkyl, phenyl, $C_7$–$C_{10}$-alkylphenyl or phenyl, phenylmethyl or phenylethyl which is substituted by one or two $C_1$–$C_4$-alkyl groups and a hydroxyl group, $R^{19}$ is hydrogen, $C_1$–$C_4$-alkyl, $C_2$–$C_{13}$-alkoxymethyl, phenyl or phenoxymethyl, $R^{20}$ is hydrogen, $C_1$–$C_{12}$-alkyl, —$CO$—$R^{18}$ or —$CO$—$N(R^{16})(R^{17})$, $R^{21}$ is $C_1$–$C_{12}$-alkyl, phenyl or $C_7$–$C_{18}$-alkylaryl, $R^{22}$ is hydrogen, $C_1$–$C_{12}$-alkyl, allyl or benzyl, $R^{23}$ is hydrogen, methyl or ethyl, $R^{24}$ and $R^{24a}$ independently of one another are H or $C_1$–$C_4$-alkyl, $R^{25}$ is hydrogen, $C_1$–$C_{12}$-alkyl, $C_3$–$C_5$-alkenyl or $C_7$–$C_{12}$-phenylalkyl, $R^{26}$ is hydrogen, $C_1$–$C_{12}$-alkyl, $C_3$–$C_8$-cycloalkyl or benzyl, and $R^{27}$ is $C_1$–$C_{12}$-alkyl, $C_5$–$C_8$-cycloalkyl or phenyl, or $R^{26}$ and $R^{27}$, together with the C atom to which they are attached, form a $C_5$–$C_{12}$-cycloalkane or $C_5$–$C_{12}$-alkylcycloalkane ring, or (c) hydrogen, $C_1$–$C_{18}$-alkyl, $C_3$–$C_6$-alkenyl, $C_7$–$C_{12}$-phenylalkyl, $C_3$–$C_{12}$-alkoxyalkyl or $C_3$–$C_{14}$-alkoxycarbonylalkyl, $R^4$ is hydrogen, $C_1$–$C_{18}$-alkyl, $C_5$–$C_8$-cycloalkyl, a group of the formula II, a group of the formula III or IV or a group —$C_mH_{2m}$—$COO(C_1$–$C_4$-alkyl) and $R^5$ is hydrogen, $C_1$–$C_{18}$-alkyl, $C_5$–$C_8$-cycloalkyl, phenyl, $C_7$–$C_9$-phenylalkyl, a group of the formula II, a group of the formula III or IV or a group of the formula V, at least one of the radicals $R^1$, $R^2$, $R^3$, $R^4$ and $R^5$ containing a sterically hindered phenol group and at least one of these radicals containing a polyalkylpiperidine group.

In these formulae, $R^{19}$, $R^{24}$ and $R^{24a}$ can be $C_1$–$C_4$-alkyl, for example methyl, ethyl, propyl, isopropyl, n-butyl, sec.-butyl or tert.-butyl. As $C_1$–$C_8$-alkyl, $R^6$, $R^7$ and $R^{17}$ can, in addition, also be, for example, isoamyl, n-hexyl, 2-ethylbutyl, n-octyl or 1,1,3,3-tetramethylbutyl. As $C_1$–$C_{12}$-alkyl, $R^9$, $R^{10}$, $R^{15}$, $R^{16}$, $R^{18}$, $R^{20}$, $R^{21}$, $R^{22}$, $R^{25}$ and $R^{26}$ can, in addition, also be, for example, nonyl, decyl or dodecyl. As $C_1$–$C_{18}$-alkyl, $R^1$, $R^2$, $R^3$, $R^4$ and $R^5$ can, in addition, also be, for example, tetradecyl, hexadecyl or octadecyl.

As $C_3$–$C_{12}$-alkoxyalkyl, $R^1$, $R^2$, $R^3$ and $R^9$ can be, for example, 2-methoxyethyl, 2-ethoxyethyl, 2-isopropoxyethyl, 3-methoxypropyl, 2-butoxyethyl, 2-butoxypropyl or 2-hexyloxyethyl. As $C_2$–$C_{13}$-alkoxymethyl, $R^{19}$ can be, for example, methoxymethyl, ethoxymethyl, butoxymethyl, 2-ethylbutoxymethyl, hexyloxymethyl or dodecyloxymethyl.

As $C_4$–$C_{12}$-dialkylaminoalkyl, $R^9$ can be, for example, 2-dimethylaminoethyl, 3-diethylaminopropyl, 2-dipropylaminoethyl or 3-dibutylaminopropyl.

As $C_3$–$C_{14}$-alkoxycarbonylalkyl, $R^1$, $R^2$ and $R^3$ can be, for example, alkoxycarbonylmethyl, 2-alkoxycarbonylethyl or 2-alkkoxycarbonylpropyl.

As $C_3$–$C_6$-alkenyl, $R^1$, $R^2$, $R^3$, $R^{10}$, $R^{18}$ and $R^{25}$ can be, in particular, $C_2$–$C_5$-alkenylmethyl, for example allyl, methallyl, 3-methylallyl or 3,3-dimethylallyl. As $C_3$–$C_4$-alkinyl, $R^{10}$ can be, for example, propargyl or 3-methylpropargyl.

As $C_5$–$C_8$-cycloalkyl, $R^4$, $R^5$, $R^6$, $R^7$, $R^{26}$ and $R^{27}$ can be, for example, cyclopentyl, cyclohexyl, methylcyclohexyl, dimethylcyclohexyl, cycloheptyl or cyclooctyl. As $C_5$–$C_{12}$-cycloalkyl, $R^9$ and $R^{18}$ can, in addition, also be, for example, cyclodecyl or cyclododecyl.

If $R^{26}$ and $R^{27}$, together with the C atom to which they are attached, form a cycloalkane or alkylcycloalkane ring, this can be, for example, a cyclopentane, cyclohexane, methylcyclohexane, dimethylcyclohexane, cycloheptane, cyclooctane or cyclododecane ring.

As $C_7$–$C_9$-phenylalkyl, $R^5$, $R^6$ and $R^7$ can be, for example, benzyl, 2-phenylethyl, 3-phenylpropyl or 1-phenylisopropyl. As $C_7$–$C_{12}$-phenylalkyl, $R^1$, $R^2$, $R^3$, $R^{10}$, $R^{18}$ and $R^{25}$ can, in addition, also be, for example, 3-phenylbutyl or 6-phenylhexyl.

As $C_7$–$C_{10}$-alkylphenyl, $R^6$, $R^7$ and $R^{18}$ can be, for example, tolyl, xylyl, ethylphenyl, isopropylphenyl or tert.-butylphenyl. As $C_7$–$C_{18}$-alkylaryl, $R^{21}$ can, in addition, also be, for example, methylnaphthyl, butylnaphthyl, nonylphenyl or dodecylphenyl.

Together with the N atom to which they are attached, $R^{16}$ and $R^{17}$ can in each case form a 5-membered or 6-membered heterocyclic ring. This can be, for example, a pyrrolidine, piperidine, morpholine or 4-methylpiperazine ring.

In the phenolic radical of the formula II, the hydroxyl group can be in the meta-position or para-position relative to the $CH_2$ group, but is preferably in the para-position. If the $CH_2$ group is in the p-position relative to the hydroxyl group, $R^8$ is in the m-position. If the $CH_2$ group is in the m-position, $R^8$ is in the p-position relative to the hydroxyl group.

Preferred stabilisers of the formula I are those in which X is a group —$N(R^3)$— or —$C(R^4)(R^5)$— and at least one of the radicals $R^1$, $R^2$, $R^3$, $R^4$ and $R^5$ contains a sterically hindered phenol group and at least one of these radicals contains an N-substituted 2,2,6,6-tetramethylpiperidine group.

Stabilisers of the formula I which are particularly preferred are those in which X is a group —$N(R^3)$— or —$C(R^4)(R^5)$— and $R^1$, $R^2$ and $R^3$ independently of one another are either (a) a group of the formula IIa or IIb

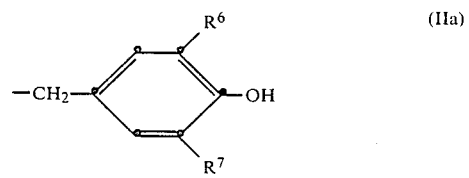

(IIa)

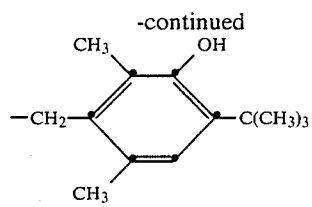

(IIb)

in which $R^6$ is hydrogen, $C_1$–$C_8$-alkyl, $C_5$–$C_8$-cycloalkyl or $C_7$–$C_9$-phenylalkyl and $R^7$ is $C_1$–$C_8$-alkyl, $C_5$–$C_8$-cycloalkyl or phenyl, or (b) a group of the formula III in which m is 1, 2 or 3, Y is —O— or —N($R^9$)— in which $R^9$ is hydrogen, $C_1$–$C_{12}$-alkyl or cyclohexyl or $R^9$ is D, D is a group of the formula V in which R is hydrogen and $R^{10}$ is $C_1$–$C_6$-alkyl, allyl, benzyl, $C_1$–$C_4$-alkyl which is substituted by —CN or —COO$R^{15}$, or a group —CO—$R^{18}$, —COO$R^{15}$, —CON($R^{16}$)($R^{17}$), —CH$_2$—CH($R^{19}$)— O$R^{20}$, —SO$R^{21}$, —SO$_2R^{21}$, —O$R^{15}$ or —OOC—$R^{18}$ in which $R^{15}$ is $C_1$–$C_8$-alkyl, $R^{16}$ is $C_1$–$C_8$-alkyl, cyclohexyl or phenyl and $R^{17}$ is hydrogen or $C_1$–$C_8$-alkyl, or $R^{16}$ and $R^{17}$, together with the N atom, are pyrrolidine, piperidine or morpholine, $R^{18}$ is $C_1$–$C_4$-alkyl, $C_2$–$C_3$-alkenyl, cyclohexyl, phenyl or benzyl, $R^{19}$ is hydrogen or methyl, $R^{20}$ is hydrogen, $C_1$–$C_8$-alkyl or a group of the formula IX

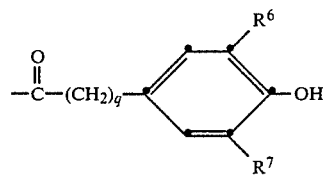

(IX)

in which q is 0, 1 or 2, and $R^{21}$ is $C_1$–$C_4$-alkyl, phenyl or p-tolyl, or (c) hydrogen, $R^4$ and $R^5$ independently of one another are hydrogen or $C_1$–$C_{12}$-alkyl or are as defined under (a) or (b), and at least one of the radicals $R^1$, $R^2$, $R^3$, $R^4$ and $R^5$ contains a sterically hindered phenol group and at least one of these radicals contains an N-substituted 2,2,6,6-tetramethylpiperidine group.

Compounds of the formula I in which X is a group —N($R^3$)— constitute isocyanuric acid esters. Preferred stabilisers within this group are those in which $R^1$ and $R^2$ are a group of the formula IIa in which $R^6$ is hydrogen or $C_1$–$C_4$-alkyl and $R^7$ is $C_1$–$C_4$-alkyl, $R^3$ is a group of the formula III in which m is 1 or 2, Y is —O— or —N($R^9$)— in which $R^9$ is hydrogen or $C_1$–$C_{12}$-alkyl or $R^9$ is D, and D is a group of the formula V in which R is hydrogen and $R^{10}$ is methyl, allyl, benzyl, acetyl, acryloyl, methoxy, ethoxy or —CH$_2$CH$_2$O$R^{20}$ in which $R^{20}$ is hydrogen or a group of the formula IX in which q is 0, 1 or 2 and $R^6$ and $R^7$ are as defined above.

Compounds of the formula I in which X is a group —C($R^4$)($R^5$)— constitute barbituric acid derivatives. Preferred stabilisers within this group are those in which $R^1$ and $R^2$ are a group of the formula IIa in which $R^6$ is hydrogen or $C_1$–$C_4$-alkyl and $R^7$ is $C_1$–$C_4$-alkyl, $R^4$ is a group of the formula III in which m is 1 or 2, Y is —O— or —N($R^9$)— in which $R^9$ is hydrogen or $C_1$–$C_{12}$-alkyl, or $R^9$ is D, and D is a group of the formula V in which R is hydrogen and $R^{10}$ is methyl, allyl, benzyl, acetyl, acryloyl, methoxy, acetoxy or —CH$_2$CH$_2$O$R^{20}$ in which $R^{20}$ is hydrogen or a group of the formula IX in which q is 0, 1 or 2, $R^6$ is hydrogen or $C_1$–$C_4$-alkyl and $R^7$ is $C_1$–$C_4$-alkyl, and $R^5$ is as defined for $R^4$ or is $C_1$–$C_{12}$-alkyl or is as defined for $R^1$, but particularly those in which $R^1$ and $R^2$ are a group of the formula III in which m is 1 or 2, Y is —O— or —N($R^9$)— in which $R^9$ is hydrogen or $C_1$–$C_{12}$-alkyl, or $R^9$ is D, and D is a group of the formula V in which R is hydrogen and $R^{10}$ is methyl, allyl, benzyl, acetyl, acryloyl, methoxy, acetoxy or —CH$_2$CH$_2$O$R^{20}$ in which $R^{20}$ is hydrogen or a group of the formula IX in which q is 0, 1 or 2, $R^6$ is hydrogen or $C_1$–$C_4$-alkyl and $R^7$ is $C_1$–$C_4$-alkyl, $R^4$ is a group of the formula IIa in which $R^6$ is $R^7$ are as defined above and $R^5$ is as defined for $R^4$ or is $C_1$–$C_{12}$-alkyl or is as defined for $R^1$.

Some of the compounds described herein of the formula I in which X is a group —N($R^3$)— are known from German Offenlegungschrift No. 2,730,397 or U.S. Pat. No. 4,317,911, where their preparation, and also their use as stabilisers for plastics, is described in detail.

Some of the compounds herein described of the formula I in which X is a group —C($R^4$)($R^5$)— are known from German Offenlegungschrift No. 2,730,503 or U.S. Pat. No. 4,185,007, where their preparation, and their use in plastics, is also described.

Insofar as the compounds described herein are novel, they can be prepared analogously to the known compounds.

Examples of individual compounds of the formula I in which X is a group —N($R^3$)— are those of the following formulae

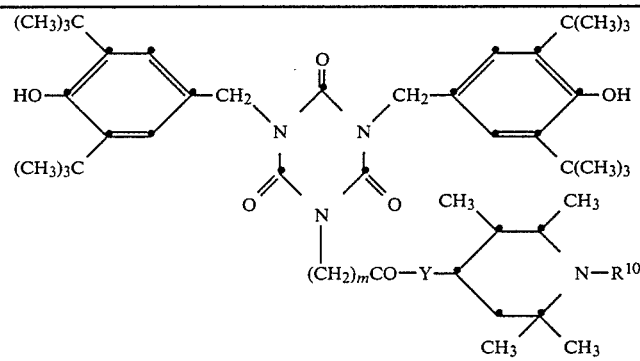

| Compound No. | m | Y | $R^{10}$ |
|---|---|---|---|
| 1 | 1 | —O— | —CO—CH=CH$_2$ |
| 2 | 1 | —O— | —CH$_3$ |

-continued
| | | | |
|---|---|---|---|
| 3 | 1 | —O— | —CH₂—C₆H₅ |
| 4 | 1 | —O— | —CO—N(C₂H₅)₂ |
| 5 | 1 | —NH— | —CO—CH=CH₂ |
| 6 | 1 | —NH— | —CO—CH₃ |
| 7 | 1 | —N(C₄H₉)— | —CO—CH₃ |
| 8 | 2 | —O— | —SO₂—C₆H₄—CH₃ |
| 9 | 2 | —NH— | —CH₂CN |
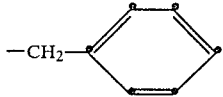
| No. | m = | Y = | R¹⁰ = |
|---|---|---|---|
| 10 | 1 | —O— | —CO—CH=CH₂ |
| 11 | 1 | —O— | —CO—N(C₂H₅)₂ |
| 12 | 1 | —O— | —CH₂—C₆H₅ |
| 13 | 1 | —O— | —CH₃ |
| 14 | 1 | —O— | —CO—CH₃ |
| 15 | 1 | —NH— | —CH₃ |
| 16 | 2 | —O— | —CO—CH=CH₂ |
| 17 | 2 | —O— | —OOC—CH₃ |
| 18 | 2 | —N(C₃H₇)— | —CO—CH₃ |
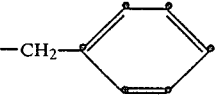
| No. | R¹⁰ = |
|---|---|
| 19 | —CH₃ |
| 20 | —CO—CH=CH₂ |
| 21 | —CH₂CH₂OOCCH₃ |

-continued
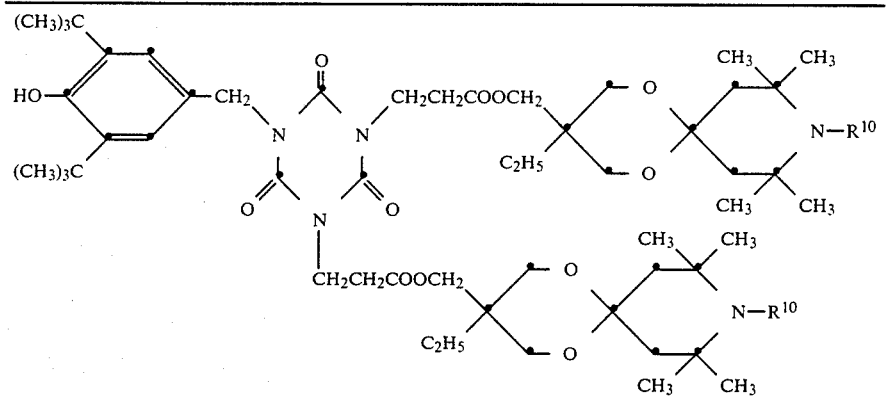
| No. | $R^{10} =$ |
|---|---|
| 22 | $-COCH_3$ |
| 23 | $-CH_2CH=CH_2$ |
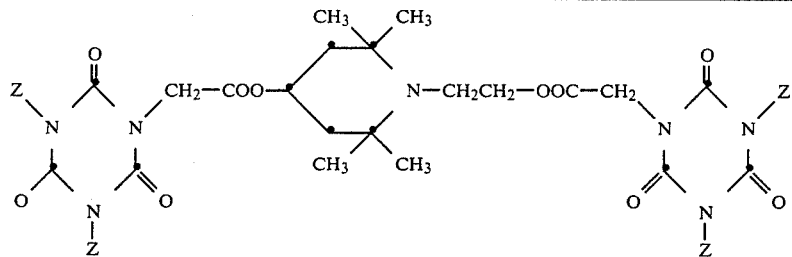
| No. | $Z =$ |
|---|---|
| 24 | 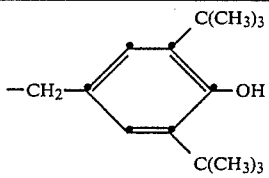 |
Examples of compounds of the formula I in which X is a group $-C(R^4)(R^5)-$ are those of the following formulae:
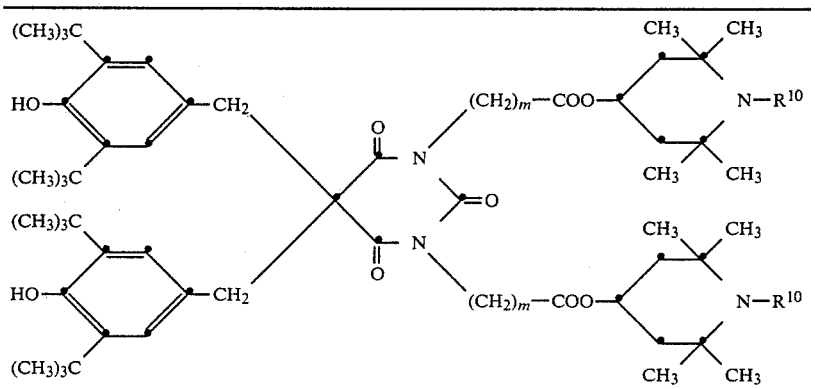
| No. | m = | $R^{10} =$ |
|---|---|---|
| 24 | 1 | $-CH_3$ |
| 26 | 1 | $-CO-CH=CH_2$ |
| 27 | 2 | $-CH_2CH=CH_2$ |

-continued
| 28 | 1 | 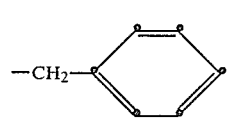 |
|---|---|---|
| 29 | 2 | —CH₃ |
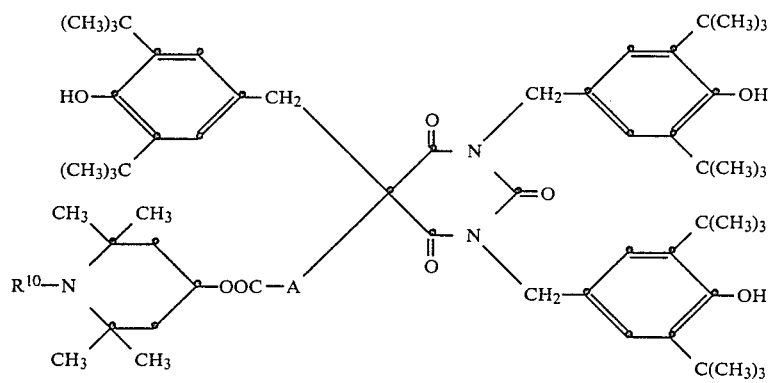
| No. | A = | R¹⁰ = |
|---|---|---|
| 30 | —CH₂— | —CO—CH=CH₂ |
| 31 | —CH₂CH₂— | —CH₃ |
| 32 | —CH(CH₃)—CH₂— | —COCH₃ |
| 33 | —CH(CH₃)—CH₂— | —CH₃ |
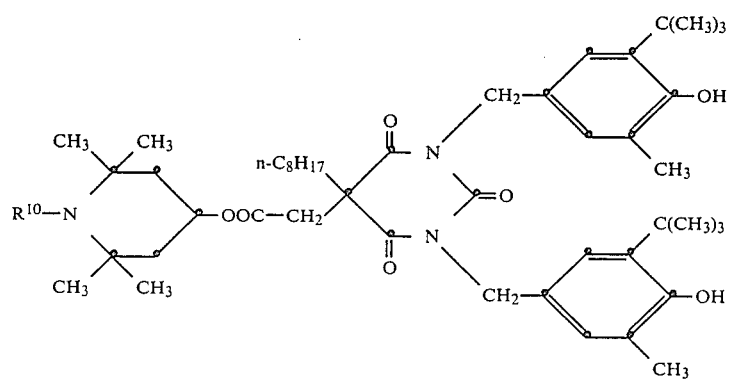
| No. | | R¹⁰ = |
|---|---|---|
| 34 | | —COCH₃ |
| 35 | | —CH₃ |
No. 36
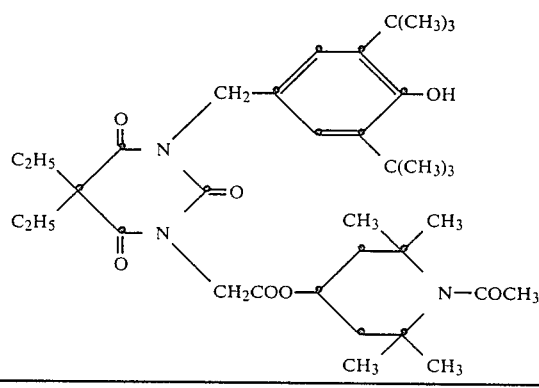

-continued

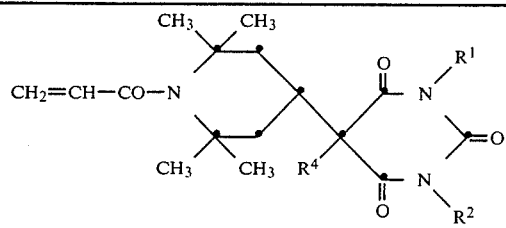

| No. | $R^1 = R^2 = R^4 =$ |
|---|---|
| 37 | 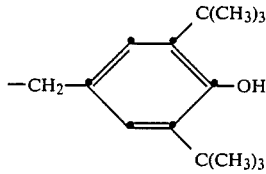 |

No. 38
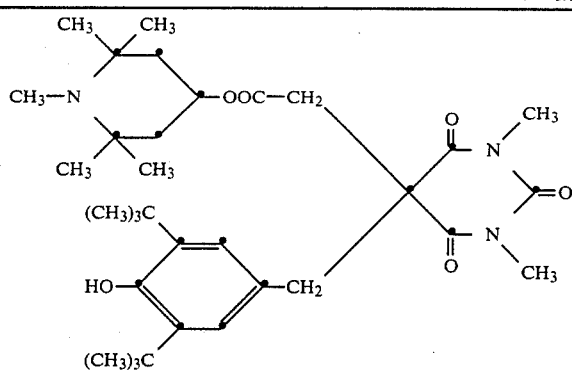

The stabilisers of the formula I can be incorporated in a known manner into a photographic material on their own or together with other compounds.

As a rule, the stabilisers are incorporated into the photographic material on their own or together with other compounds, particularly with the colour couplers, in the form of a dispersion, this dispersion either containing no solvent or high-boiling or low-boiling solvents or a mixture of such solvents. A further suitable mode of incorporation consists in incorporating the stabilisers, on their own or together with further compounds, together with a polymer in the form of a latex into the photographic material.

The dispersions are then used to prepare the layers of colour-photographic recording materials. These layers can be, for example, intermediate layers or protective layers, but particularly light-sensitive (blue-, green- and red-sensitive) silver halide emulsion layers, in which the blue-green (cyan) dyes, purple (magenta) dyes and yellow dyes are formed from the appropriate colour couplers when the exposed recording material is developed.

The silver halide layers can contain any desired colour couplers, particularly blue-green, purple and yellow couplers, which are used to form the said dyes and thus the dye images.

Since the substrate affects the action and stability of the stabilisers, preferred substrates (solvents or polymers) are those which, together with the stabilisers, produce the best possible stability in the materials to be stabilised.

As a rule, the stabilisers are incorporated into layers containing, in addition, a silver halide dispersion which has been prepared and sensitised by conventional methods. They can, however, also be present in layers which are adjacent to layers containing silver halide.

The photographic materials according to the invention have a conventional composition and contain components which enhance, or at least do not adversely affect, the activity of the stabilisers.

In the photographic recording material according to the present invention, the stabilisers of the formula I can be combined in the same layer not only with the colour couplers, but also, in addition, with ultraviolet absorbers or other light stabilisers.

If the diffusion transfer method is used, the stabiliser can also be incorporated in a receiving layer.

The colour-photographic materials according to the invention can be processed in a known manner. Furthermore, they can be treated in the course of, or after, processing in a manner which increases their stability further, for example by treatment in a stabiliser bath or by the application of a protective coating.

In certain cases, the stabilisers which can be employed in accordance with the invention are also suitable for protecting colour-photographic layers in which the dyes are directly incorporated in the emulsion and the image is produced by selective bleaching.

The amount of the stabiliser or stabilisers can vary within wide limits and is approximately within the range from 1 to 2,000 mg, preferably 100 to 800 and, in particular, 200–500 mg, per m² of the layer in which it (they) is (are) incorporated.

If the photographic material contains one or more UV absorbers, the latter can be present together with the stabiliser in one layer or can also be present in an adjacent layer. The amount of UV absorber can vary within wide limits and is approximately within the range from 200 to 2,000 mg, preferably 400–1,000 mg, per m² of layer. Examples of suitable UV absorbers are those of the benzophenone, acrylonitrile, thiazolidone, benztriazole, oxazole, thiazole and imidazole type.

The colour images obtained with the recording material according to the invention by exposure and development have a very good light-fastness towards visible and ultraviolet light. The compounds of the formula I are virtually colourless, so that no discolouration of the images results; in addition, they are readily compatible with the customary photographic additives present in the individual layers. By virtue of their good activity, it is possible to reduce the quantity of them employed and thus to prevent them from being precipitated or crystallising out if they are incorporated as an organic solution into the aqueous binder emulsions which are used for the preparation of photographic layers. The individual processing stages required, after the exposure of the photographic recording material, for the production of the colour images are not adversely affected by the stabilisers of the formula I. Furthermore, the so-called formation of abrasion fogging which frequently occurs with blue-sensitive emulsions is substantially repressed. This can occur, for example, if mechanical stresses, for example twisting, bending or rubbing, are exerted on photographic materials (silver halide emulsion layers located on a base composed of natural or synthetic materials) while they are being prepared or treated before being developed. (T. H. James, The Theory of Photographic Process, 4th edition, Macmillan, New York, NY 1977, pages 23 et seq and 166 et seq).

EXAMPLE 0.087 g of the yellow coupler of the formula

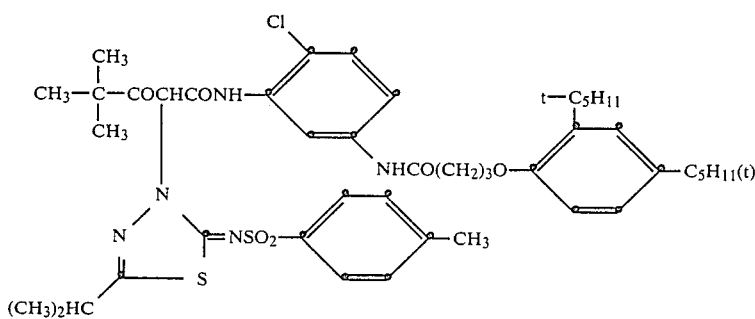

and 0.026 g of one of the stabilisers indicated in the Table below are dissolved in 2.0 ml of a mixture of tricresyl phosphate and ethylacetate (1.5 g in 100 ml). 7.0 ml of a 6% gelatin solution, 0.5 ml of an 8% solution of the wetting agent of the formula

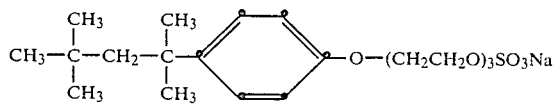

in isopropanol/water (3:4) and 0.5 ml of water are added to this solution, and the mixture is emulsified by ultrasonic means at an input of 100 watts for 5 minutes.

2.0 ml of a silver bromide emulsion having a silver content of 6.0 g per liter, 0.7 ml of a 1% aqueous solution of the hardener of the formula

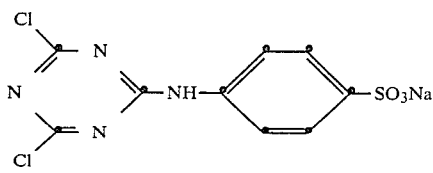

and 3.8 ml of water are added to 2.5 ml of the emulsion thus obtained, the pH of the mixture is adjusted to a value of 6.5 and is coated onto a subbed, plastic-coated, white sheet of paper, mounted on a glass plate.

After the mixture has solidified, it is dried at room temperature in a circulating air drying cabinet.

After 7 days, samples cut to dimensions of 35×180 mm are exposed at 3,000 lux.second behind a stepped wedge and are then processed by the Kodak Ektaprint ® 2-staged process.

The yellow wedges thus obtained are irradiated at a total of 42 kJoules/cm² in an Atlas weather-ometer using a 2,500 watt xenon lamp (a comparison sample contains no light stabiliser). The loss of colour density thereby occasioned is determined by measuring the colour density at $\lambda_{max}$ using a densitometer (TR 924 A made by Macbeth).

The results are shown in the Table below.

| Stabiliser Compound No. | Percentage loss of colour density |
| --- | --- |
| 1 | 20 |
| 3 | 22 |
| 4 | 21 |
| 5 | 22 |
| 12 | 20 |
| 13 | 16 |
| 14 | 20 |
| 20 | 22 |
| without stabiliser | 36 |

What we claim is:

1. A colour-photographic recording material which, in at least one light-sensitive silver halide emulsion layer, one intermediate layer, one image-receiving layer and/or one protective layer, contains, as a stabiliser, a light stabilising amount of at least one compound of the formula I 4,518,688

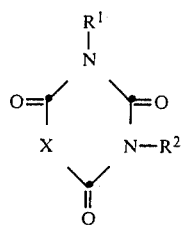

(I)

in which X is a group

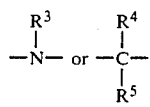

and $R^1$, $R^2$, $R^3$, $R^4$ and $R^5$ are monovalent organic radicals, at least one of which contains a sterically hindered phenol group and at least one of which contains a polyalkylpiperidine group.

2. A colour-photographic recording material according to claim 1, containing at least one compound of the formula I in which X is a group —$N(R^3)$— or —$C(R^4)(R^5)$—, $R^1$, $R^2$ and $R^3$ independently of one another are either (a) a group of the formula II

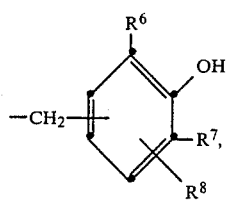

(II)

in which $R^6$ is hydrogen, $C_1$–$C_8$-alkyl, $C_5$–$C_8$-cycloalkyl, $C_7$–$C_9$-phenylalkyl, phenyl or $C_7$–$C_{10}$-alkylphenyl, $R^7$ is $C_1$–$C_8$-alkyl, $C_5$–$C_8$-cycloalkyl, $C_7$–$C_9$-phenylalkyl, phenyl or $C_7$–$C_{10}$-alkylphenyl, and $R^8$ is hydrogen or methyl, or (b) a group of the formula III or IV —$C_mH_{2m}$—CO—Y—D (III)

—$C_mH_{2m}$—CO—O—$C_nH_{2n}$—E (IV)

in which m is 1–4 and n is 2–5, Y is —O— or —$NR^9$— and $R^9$ is hydrogen, $C_1$–$C_{12}$-alkyl, $C_5$–$C_{12}$-cycloalkyl, $C_3$–$C_{12}$-alkoxyalkyl, $C_4$–$C_{12}$-dialkylaminoalkyl or a group of the formula

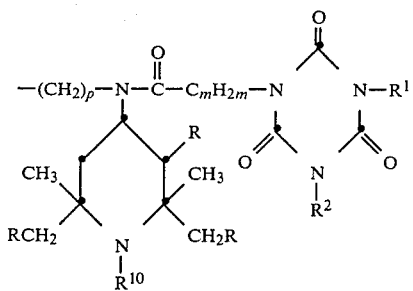

in which p is 2–12, or $R^9$ is D, D is a group of the formula V, VI or VIII

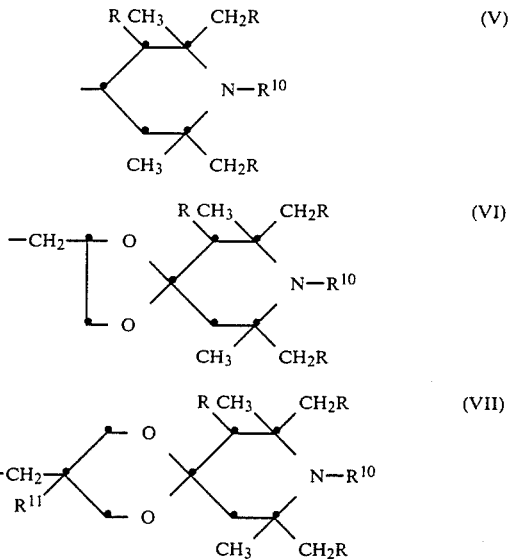

(V)

(VI)

(VII)

and E is a group of the formula VIII

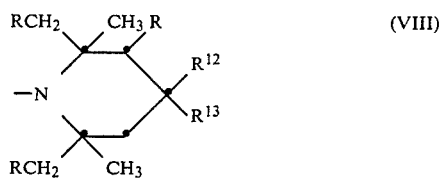

(VIII)

in which R is hydrogen or methyl, $R^{10}$ is hydroxyl, $C_1$–$C_{12}$-alkyl, $C_3$–$C_6$-alkenyl, $C_3$–$C_4$-alkinyl, $C_7$–$C_{12}$-phenylalkyl, glycidyl, $C_1$–$C_4$-alkyl which is substituted by halogen, —CN, —$COOR^{15}$ or —$CON(R^{16})(R^{17})$, or a group —CO—$R^{18}$ —CO—$OR^{15}$, —CO—$N(R^{16}(R^{17}))$, —$CH_2$—$CH(R^{19})$—$OR^{20}$, —SO—$R^{21}$, —$SO_2$—$R^{21}$, —$OR^{15}$ or —OOC—$R^{18}$, $R^{11}$ is methyl or ethyl, $R^{12}$ is hydrogen, —$OR^{22}$, —OOC—$R^{18}$ or —$N(R^9)$—CO—$R^{18}$ and $R^{13}$ is hydrogen, —CN, —$COOR^{15}$ or —$CONH_2$ or $R^{12}$ and $R^{13}$ together form a group of the following formulae

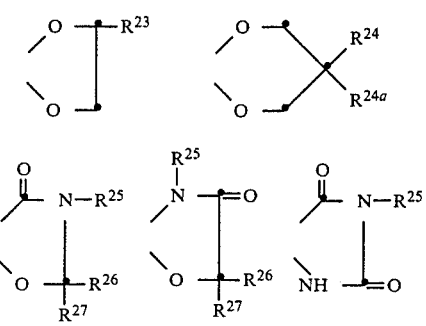

$R^{15}$ is $C_1$–$C_{12}$-alkyl, allyl, benzyl or cyclohexyl, $R^{16}$ is $C_1$–$C_{12}$-alkyl, allyl, cyclohexyl, benzyl or phenyl, and $R^{17}$ is hydrogen or $C_1$–$C_8$-alkyl, or $R^{16}$ and $R^{17}$, together with the N atom, are a 5-membered or 6-membered heterocyclic ring, $R^{18}$ is hydrogen, $C_1$–$C_{12}$-alkyl, $C_2$–$C_6$-alkenyl, chloromethyl, $C_5$–$C_{12}$-cycloalkyl, $C_7$–$C_{12}$-phenylalkyl, phenyl, $C_7$–$C_{10}$-alkylphenyl or phenyl, phenylmethyl or phenylethyl which is substituted by one or two $C_1$–$C_4$-alkyl groups and a hydroxyl group, $R^{19}$ is hydrogen, $C_1$-$C_4$-alkyl, $C_2$-$C_{13}$-alkoxymethyl, phenyl or phenoxymethyl, $R^{20}$ is hydrogen, $C_1$-$C_{12}$-alkyl, —CO—$R^{18}$ or —CO—N($R^{16}$)($R^{17}$), $R^{21}$ is $C_1$-$C_{12}$-alkyl, phenyl or $C_7$-$C_{18}$-alkylaryl, $R^{22}$ is hydrogen, $C_1$-$C_{12}$-alkyl, allyl or benzyl, $R^{23}$ is hydrogen, methyl or ethyl, $R^{24}$ and $R^{24a}$ independently of one another are H or $C_1$-$C_4$-alkyl, $R^{25}$ is hydrogen, $C_1$-$C_{12}$-alkyl, $C_3$-$C_6$-alkenyl or $C_7$-$C_{12}$-phenylalkyl, $R^{26}$ is hydrogen, $C_1$-$C_{12}$-alkyl, $C_3$-$C_8$-cycloalkyl or benzyl, and $R^{27}$ is $C_1$-$C_{12}$-alkyl, $C_5$-$C_8$-cycloalkyl or phenyl, or $R^{26}$ and $R^{27}$, together with the C atom to which they are attached, form a $C_5$-$C_{12}$-cycloalkane or $C_5$-$C_{12}$-alkylcycloalkane ring, or (c) hydrogen, $C_1$-$C_{18}$-alkyl, $C_3$-$C_6$-alkenyl, $C_7$-$C_{12}$-phenylalkyl, $C_3$-$C_{12}$-alkoxyalkyl or $C_3$-$C_{14}$-alkoxycarbonylalkyl, $R^4$ is hydrogen, $C_1$-$C_{18}$-alkyl, $C_5$-$C_8$-cycloalkyl, a group of the formula II, a group of the formula III or IV or a group —$C_mH_{2m}$—COO($C_1$-$C_4$-alkyl) and $R^5$ is hydrogen, $C_1$-$C_{18}$-alkyl, $C_5$-$C_8$-cycloalkyl, phenyl, $C_7$-$C_9$-phenylalkyl, a group of the formula II, a group of the formula III or IV or a group of the formula V, at least one of the radicals $R^1$, $R^2$, $R^3$, $R^4$ and $R^5$ containing a sterically hindered phenol group and at least one of these radicals containing a polyalkylpiperidine group.

3. A colour-photographic recording material according to claim 1, containing at least one compound of the formula I in which X is a group —N($R^3$)— or —C($R^4$)($R^5$)—, and at least one of the radicals $R^1$, $R^2$, $R^3$, $R^4$ and $R^5$ contains a sterically hindered phenol group and at least one of the radicals contains an N-substituted 2,2,6,6-tetramethylpiperidine group.

4. A colour-photographic recording material according to claim 2, containing a compound of the formula I in which X is a group —N($R^3$)— or —($R^4$)($R^5$)—, and $R^1$, $R^2$ and $R^3$ independently of one another are either (a) a group of the formula IIa or IIb

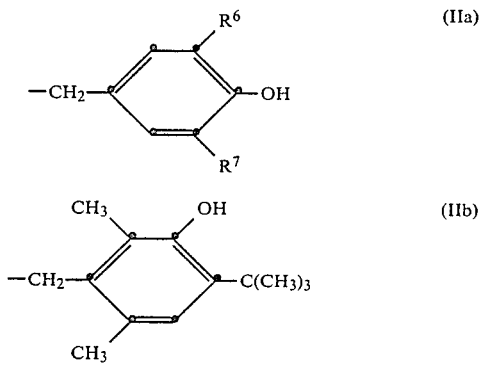

in which $R^6$ is hydrogen, $C_1$-$C_8$-alkyl, $C_5$-$C_8$-cycloalkyl or $C_7$-$C_9$-phenylalkyl and $R^7$ is $C_1$-$C_8$-alkyl, $C_5$-$C_8$-cycloalkyl or phenyl, or (b) a group of the formula III in which m is 1, 2 or 3, Y is —O— or —N($R^9$)— in which $R^9$ is hydrogen, $C_1$-$C_{12}$-alkyl or cyclohexyl or $R^9$ is D, D is a group of the formula V in which R is hydrogen and $R^{10}$ is $C_1$-$C_6$-alkyl, allyl, benzyl, $C_1$-$C_4$-alkyl which is substituted by —CN or —COO$R^{15}$, or a group —CO—$R^{18}$, —COO$R^{15}$, —CON($R^{16}$)($R^{17}$), —$CH_2$—CH($R^{19}$)—O$R^{20}$, —SO$R^{21}$, —$SO_2R^{21}$, —O$R^{15}$ or —OOC—$R^{18}$ in which $R^{15}$ is $C_1$-$C_8$-alkyl, $R^{16}$ is $C_1$-$C_8$-alkyl, cyclohexyl or phenyl and $R^{17}$ is hydrogen or $C_1$-$C_8$-alkyl, or $R^{16}$ and $R^{17}$, together with the N atom, are pyrrolidine, piperidine or morpholine, $R^{18}$ is $C_1$-$C_4$-alkyl, $C_2$-$C_3$-alkenyl, cyclohexyl, phenyl or benzyl, $R^{19}$ is hydrogen or methyl, $R^{20}$ is hydrogen, $C_1$-$C_8$-alkyl or a group of the formula IX

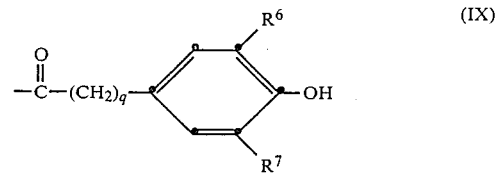

in which q is 0, 1 or 2, and $R^{21}$ is $C_1$-$C_4$-alkyl, phenyl or p-tolyl, or (c) hydrogen, $R^4$ and $R^5$ independently of one another are hydrogen or $C_1$-$C_{12}$-alkyl or are as defined under (a) or (b), and at least one of the radicals $R^1$, $R^2$, $R^3$, $R^4$ and $R^5$ contains a sterically hindered phenol group and at least one of these radicals contains an N-substituted 2,2,6,6-tetramethylpiperidine group.

5. A colour-photographic recording material according to claim 4, containing a compound of the formula I in which X is a group —N($R^3$)—, in which $R^1$ and $R^2$ are a group of the formula IIa in which $R^6$ is hydrogen or $C_1$-$C_4$-alkyl and $R^7$ is $C_1$-$C_4$-alkyl, $R^3$ is a group of the formula III in which m is 1 or 2, Y is —O— or —N($R^9$)— in which $R^9$ is hydrogen or $C_1$-$C_{12}$-alkyl or $R^9$ is D, and D is a group of the formula V in which R is hydrogen and $R^{10}$ is methyl, allyl, benzyl, acetyl, acryloyl, methoxy, ethoxy or —$CH_2CH_2OR^{20}$ in which $R^{20}$ is hydrogen or a group of the formula IX in which q is 0, 1 or 2 and $R^6$ and $R^7$ are as defined above.

6. A colour-photographic recording material according to claim 4, containing a compound of the formula I in which X is a group —C($R^4$)($R^5$)—, $R^1$ and $R^2$ are a group of the formula IIa in which $R^6$ is hydrogen or $C_1$-$C_4$-alkyl and $R^7$ is $C_1$-$C_4$-alkyl, $R^4$ is a group of the formula III in which m is 1 or 2, Y is —O— or —N($R^9$)— in which $R^9$ is hydrogen or $C_1$-$C_{12}$-alkyl, or $R^9$ is D, and D is a group of the formula V in which R is hydrogen and $R^{10}$ is methyl, allyl, benzyl, acetyl, acryloyl, methoxy, acetoxy or —$CH_2CH_2OR^{20}$ in which $R^{20}$ is hydrogen or a group of the formula IX in which q is 0, 1 or 2, $R^6$ is hydrogen or $C_1$-$C_4$-alkyl and $R^7$ is $C_1$-$C_4$-alkyl, and $R^5$ is as defined for $R^4$ or is $C_1$-$C_{12}$-alkyl or is as defined for $R^1$.

7. A colour-photographic recording material according to claim 4, containing a compound of the formula I in which X is a group —C($R^4$)($R^5$)—, $R^1$ and $R^2$ are a group of the formula III in which m is 1 or 2, Y is —O— or —N($R^9$)— in which $R^9$ is hydrogen or $C_1$-$C_{12}$-alkyl, or $R^9$ is D, and D is a group of the formula V in which R is hydrogen and $R^{10}$ is methyl, allyl, benzyl, acetyl, acryloyl, methoxy, acetoxy or —$CH_2CH_2OR^{20}$ in which $R^{20}$ is hydrogen or a group of the formula IX in which q is 0, 1 or 2, $R^6$ is hydrogen or $C_1$-$C_4$-alkyl and $R^7$ is $C_1$-$C_4$-alkyl, $R^4$ is a group of the formula IIa in which $R^6$ and $R^7$ are as defined above and $R^5$ is as defined for $R^4$ or is $C_1$-$C_{12}$-alkyl or is as defined for $R^1$.

8. A colour-photographic recording material according to claim 1, which, in addition to a stabiliser of the formula I contains a light stabiliser belonging to the class comprising the ultraviolet absorbers.

9. A colour-photographic recording material according to claim 1, which contains 1 to 2,000 mg per $m^2$ of a compound of the formula I.

10. A colour-photographic recording material according to claim 9 which contains 100 to 800 mg per $m^2$ of a compound of the formula I.

* * * * *